US005706997A

United States Patent [19]
Green et al.

[11] Patent Number: 5,706,997
[45] Date of Patent: *Jan. 13, 1998

[54] APPARATUS FOR APPLYING SURGICAL FASTENERS

[75] Inventors: David T. Green, Westport; Henry Bolanos, East Norwalk; Keith Ratcliff, Sandy Hook; Lisa W. Heaton, Norwalk; Frank J. Viola, Sandy Hook, all of Conn.

[73] Assignee: United States Surgical Corporation, Norwalk, Conn.

[*] Notice: The portion of the term of this patent subsequent to Jan. 10, 2014, has been disclaimed.

[21] Appl. No.: 474,504

[22] Filed: Jun. 7, 1995

Related U.S. Application Data

[63] Continuation of Ser. No. 179,776, Jan. 10, 1994, Pat. No. 5,509,596, which is a continuation of Ser. No. 779,097, Oct. 18, 1991, abandoned.

[51] Int. Cl.[6] .................................................. A61B 17/072
[52] U.S. Cl. .................................. 227/175.2; 227/176.1; 227/19
[58] Field of Search ............................. 227/175.1, 176.1, 227/19, 30, 181.1, 175.2

[56] References Cited

U.S. PATENT DOCUMENTS

| 804,229 | 11/1905 | Hutchinson . |
|---|---|---|
| 2,891,250 | 6/1959 | Hirata . |
| 3,079,608 | 3/1963 | Babkin . |
| 3,080,564 | 3/1963 | Strekopitov et al. . |
| 3,252,643 | 5/1966 | Strekopytov et al. . |
| 3,269,630 | 8/1966 | Fleischer . |
| 3,593,903 | 7/1971 | Astafiev et al. . |
| 3,692,224 | 9/1972 | Astafiev et al. . |
| 3,795,034 | 3/1974 | Strekopytov et al. . |
| 4,349,028 | 9/1982 | Green . |
| 4,354,628 | 10/1982 | Green . |
| 4,442,964 | 4/1984 | Becht . |
| 4,470,533 | 9/1984 | Schuler . |

(List continued on next page.)

FOREIGN PATENT DOCUMENTS

| 0136950 | 4/1985 | European Pat. Off. . |
|---|---|---|
| 0220029 | 4/1987 | European Pat. Off. . |
| 0273468 | 7/1988 | European Pat. Off. . |
| 2542188 | 3/1983 | France . |
| 1835500 | 4/1961 | Germany ........................ 227/176 |
| 119846 | 1/1959 | U.S.S.R. . |
| 1555455 | 11/1979 | United Kingdom . |
| 2141066 | 12/1984 | United Kingdom . |

*Primary Examiner*—Rinaldi I. Rada
*Assistant Examiner*—Clark F. Dexter

[57] ABSTRACT

A surgical stapling or fastening instrument for applying surgical fasteners to tissue having an adjustable closure mechanism to linearly approximate the distance between the jaw members of the instrument. The adjustable closure mechanism consists of an advancing mechanism and a retaining mechanism, wherein the actuating mechanism is actuable to urge the jaw members towards each other. A coupling arrangement is also provided which permits firing of the staples or fasteners only when the jaw members are approximated a predetermined distance from each other.

35 Claims, 16 Drawing Sheets

U.S. PATENT DOCUMENTS

| | | |
|---|---|---|
| 4,506,670 | 3/1985 | Crossley . |
| 4,508,253 | 4/1985 | Green . |
| 4,513,746 | 4/1985 | Aranyi et al. . |
| 4,527,724 | 7/1985 | Chow et al. . |
| 4,530,453 | 7/1985 | Green . |
| 4,566,620 | 1/1986 | Green et al. . |
| 4,573,622 | 3/1986 | Green . |
| 4,580,712 | 4/1986 | Green . |
| 4,585,153 | 4/1986 | Failla et al. . |
| 4,591,085 | 5/1986 | Di Giovanni . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,632,290 | 12/1986 | Green et al. . |
| 4,715,520 | 12/1987 | Roehr, Jr. et al. . |
| 4,728,020 | 3/1988 | Green et al. . |
| 4,788,978 | 12/1988 | Strekopytov et al. . |
| 4,848,637 | 7/1989 | Pruitt . |
| 4,869,414 | 9/1989 | Green et al. . |
| 4,930,503 | 6/1990 | Pruitt . |
| 4,941,623 | 7/1990 | Pruitt . |
| 4,978,049 | 12/1990 | Green . |
| 4,994,065 | 2/1991 | Gibbs et al. . |
| 5,027,834 | 7/1991 | Pruitt . |
| 5,040,715 | 8/1991 | Green et al. . |
| 5,100,042 | 3/1992 | Gravener et al. . |
| 5,137,198 | 8/1992 | Nobis et al. . |
| 5,190,203 | 3/1993 | Rodak . |
| 5,240,163 | 8/1993 | Stein et al. . |

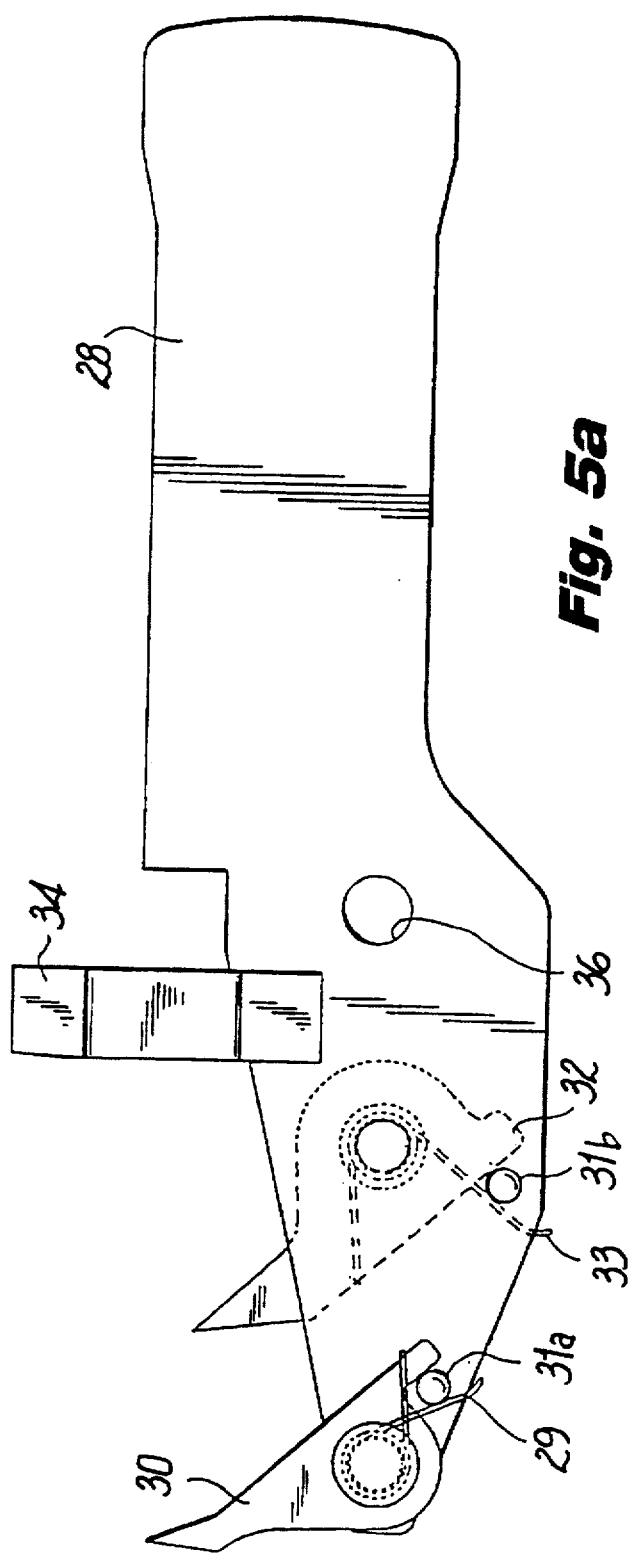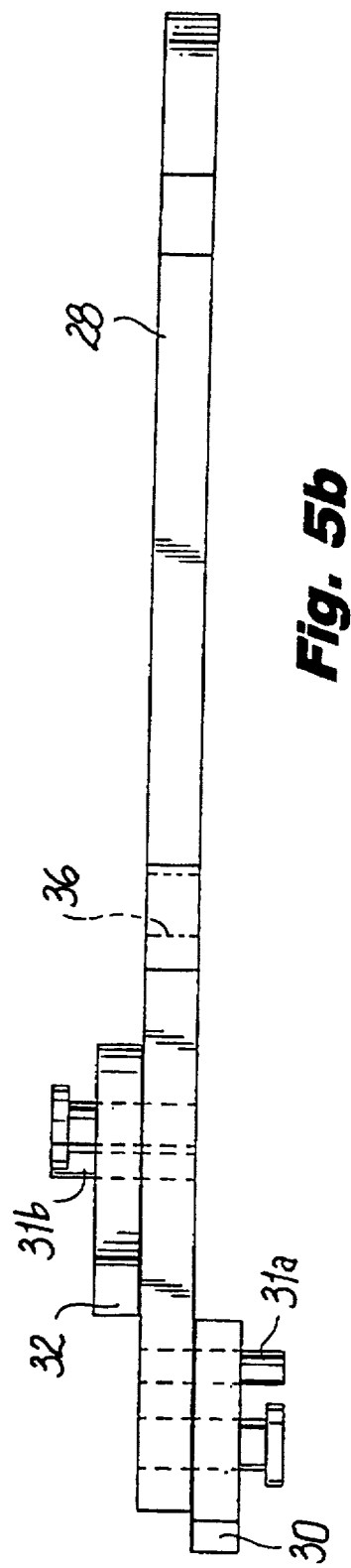

APPARATUS FOR APPLYING SURGICAL FASTENERS

This is a continuation of application Ser. No. 08/179,776 filed Jan. 10, 1994, now U.S. Pat. No. 5,509,596, which is a continuation of application Ser. No. 07/779,097 filed Oct. 18, 1991, now abandoned.

BACKGROUND OF THE INVENTION

1. Field of the Invention

The present invention relates to surgical instruments for applying surgical fasteners or staples to body tissue, and more particularly to an apparatus for applying surgical fasteners having adjustable mechanisms for controlling the spacing between the jaw members through which the tissue passes during the fastening or stapling procedures.

2. Discussion of the Related Art

Surgical fastening devices having means for controlling the spacing between the jaw members are well known in the art. These devices typically include indicating means to provide a reading of the spacing between the jaw members. Devices are also known in the art which provide latching mechanisms to actuate the firing mechanism only when the distance between the jaws is within a preset range. These devices typically include a complex lock-out mechanism.

Various closing mechanisms are provided in the prior art for use with surgical fastening devices. The most notable of these devices utilize a complex worm gear-type arrangement or screw bearing member to open and close the spacing between the jaw members of the surgical fastening apparatus. These devices generally provide a rotatable knob or wing-like assembly at the trigger end of the device remote from the jaw mechanism which carries the fastener cartridge, and a screw-like mechanism is provided that passes through the body of the device to translate the rotational movement of the knob into longitudinal movement of the cartridge frame to open and close the spacing between the jaws. As the jaw members are closed around a tissue site to which fasteners are to be applied, the surgeon must grasp the device with one hand while rotating the knob or wing-like assembly with the other hand. As the jaws members close about the tissue to pinch the tissue therebetween, the surgeon then ceases rotation and activates the trigger mechanism to drive the fasteners into the tissue. Several known devices provide a trigger-like mechanism, while others provide a secondary rotatable knob for driving the fasteners by rotational movement. Many devices provide an indicator means near the rotatable knob which gives a visual indication of the spacing between the jaw members prior to firing.

These prior art devices are subject to several disadvantages in both use and construction which render these devices difficult to operate and expensive to manufacture. Many of the devices are cumbersome in use in that the surgeon must operate the device with both hands, holding the body of the instrument in one hand while rotating the knob or wing assembly with the other hand. This may lead to inaccurate stapling or fastening since the surgeon is unable to guide the tissue to be stapled or fastened with his free hand while closing the jaws about the tissue. Furthermore, the number of interacting components provides inaccuracies due to normal break down of tolerances. In addition, the gear arrangement may become worn during extended use, thus rendering an imprecise grasping action at the jaws.

Furthermore, these prior art devices generally involve a complex construction in which a precisely machined or cast worm gear must be constructed and incorporated into the device. This of course increases the cost of manufacturing, and requires a sophisticated assembly procedure to properly locate the worm gear in the instrument to control the spacing between the jaws.

Typical devices having a rotatable knob at the end portion adjacent the handle mechanism of the surgical stapling or fastening device are disclosed in, among others, U.S. Pat. No. 4,930,503 to Pruitt, U.S. Pat. No. 4,788,978 to Strekopytov et at., and U.S. Pat. No. 4,606,344 to DiGiovanni. In each of these devices, an elongated rod member having screw threads machined thereon is provided, which connects a rotatable knob positioned adjacent the handle members to a pusher mechanism which urges a movable jaw in a forward direction toward a stationary jaw to close the spacing between the jaw members. When a desired spacing is reached, a trigger mechanism may be activated to fire the fasteners through the tissue into the anvil member mounted on the stationary jaw. To remove the fastening instrument after application of the fasteners, the knob is rotated in an opposite direction which turns the screw threaded rod member to move the movable jaw member away from the stationary jaw member so that the entire device maybe removed from the tissue.

Surgical fastening instruments having a wing like arrangement positioned adjacent the handle assembly of a device for moving a movable jaw toward a stationary jaw for affixing surgical fasteners to tissue are disclosed in U.S. Pat. No. 4,442,964 to Becht, U.S. Pat. No. 4,354,628 to Green, and U.S. Pat. No. 3,795,034 to Strekopytov et at. These devices are similar to those described above except for the provision of a rotatable wing member in place of the rotatable knob. These devices are also provided with a screw threaded red member which, when rotated, urges a movable jaw towards a stationary jaw to close the jaw members around tissue to be fastened together. After the application of surgical fasteners, the wing assembly is rotated in an opposite direction to draw the movable jaw away from the stationary jaw so that the instrument maybe removed from the tissue.

Surgical stapling of fastening instruments having a pivotable mechanism external to the device for moving a movable jaw toward a stationary jaw prior to affixing surgical fasteners to tissue are disclosed in, among others, U.S. Pat. No. 3,269,630 to Fleischer, U.S. Pat. No. 4,530,453 to Green, U.S. Pat. No. 4,715,520 to Roehr, Jr. et al., and U.S. Pat. No. 4,978,049 to Green.

Green ('453), Roehr, Jr. et al. and Green ('049) each disclose a pivotable lever member which urges a movable jaw into proximity of a stationary jaw prior to application of the surgical fasteners. Fleischer discloses a surgical stapling instrument in which a pivotable handle urges the movable staple cartridge against the tissue in the direction of the stationary jaw and fires the staples in the same motion. In each of these devices, removal of the instrument after firing of the surgical fasteners is accomplished by pivoting the lever mechanism in the opposite direction to open the jaw members by moving the movable jaw away from the stationary jaw.

U.S. Pat. No. 5,190,203 to Rodak, filed Oct. 5, 1990, discloses a spring biased pivotal catch member for approximating the jaws which is held in selected positions by a pointed lace member.

The novel surgical stapling or surgical fastening device of the present invention obviates the disadvantages encountered in the prior art and provides an efficient surgical fastening device having an adjustable closure mechanism for controlling the spacing between the jaw members of the surgical fastening apparatus. The device of the present invention allows a surgeon to operate a surgical fastener with one hand while freeing the other hand to assist in the surgical procedure. Furthermore, the present invention provides a novel means for coupling the fastener driving mechanism to the firing mechanism when the jaws are approximated to a preset distance. The device of the present invention is of lightweight construction and provides ease of handling through the provision of a thumb controlled adjustable closure mechanism which permits a surgeon to set the spacing between the jaw members and fire the device while using only one hand.

SUMMARY OF THE INVENTION

The present invention provides a surgical fastening device having a novel mechanism for adjusting the distance between the movable jaw and the stationary jaw prior to the application of fasteners to the body tissue. The adjustable mechanism controls the closing of the jaw mechanism to approximate the distance between the jaw members prior to activation of the trigger mechanism to fire the fasteners. The device of the present invention may be operated with one hand, which frees the surgeon to accurately locate the tissue to be repaired and to place the fasteners in the proper position during the procedure. The adjustable closure mechanism is operable by using the thumb of the hand which holds the device, and linearly moves the stapling mechanism to properly approximate the distance between the jaw members. The adjustable closure mechanism of the present invention eliminates many moving parts associated with prior devices, and provides a device which is lightweight, and easy to use by allowing the surgeon to set and release the device with one hand.

The adjustable closure mechanism of the present invention may be used with any surgical instrument having jaw members which include a stationary jaw and a movable jaw, or two movable jaws, in which the spacing between the jaw members is adjustable to accommodate various thicknesses of tissue to be secured. The provision of the approximating actuator at the handle end of the instrument and the elimination of numerous complex moving parts which are common in prior art devices allows the surgeon to approximate the distance between the jaw members in a fast and efficient manner to position the jaws in the proper alignment for the application of surgical fasteners.

The apparatus of the present invention comprises a first jaw member and a second jaw member in which the first jaw member includes a plurality of fastener means positioned in a cartridge which is movable with the first jaw member towards the stationary second jaw member. The second jaw member may include an anvil surface for clinching the fasteners, or may include means for engaging the fasteners to secure the tissue therebetween. Means for advancing the first jaw member towards the second jaw member to grip the tissue between the jaws are provided, as well as releasable means for retaining the advancing means along a linear path of travel to selectively position the first jaw member in relation to the second jaw member. Means for driving the fasteners into the tissue subsequent to positioning the jaw members in relation to each other by the advancement means is also provided, and the advancement means of the apparatus of the present invention is independent of the driving means.

The present invention provides an adjustable closure mechanism for a surgical fastener applying apparatus in which the closure mechanism involves a two-step procedure to approximate the distance between the jaws to grip tissue therebetween. The two-step approximating process may be performed with one hand, since the two-step process is performed using the same mechanism. In a first embodiment of the present invention, a pusher bar mechanism comprising the advancing means is also provided; however, the pusher bar mechanism is pivotably actuable to provide for approximation of the jaw members over a large distance, and is also pivotably actuable to provide for incremental adjustment of the gap between the jaws following the initial approximation. In this embodiment, the pusher bar mechanism is not linearly slidable, but instead only pivots to provide for approximation of the distance between the jaw members. A pair of pawl members are provided on the pusher bar mechanism which engage a corresponding pair of ratchet members positioned on a movable rod which moves the cartridge frame and the fastener driver, which both cooperate with the movable cartridge jaw. In order to approximate the gap between the jaw members, the pusher bar mechanism is pivotably pushed in a downward, "pumping" motion so that the first advancing means advances the cartridge jaw a large distance. The first advancing means comprises a pawl member positioned on the pusher bar mechanism which engages a ratchet member positioned on the movable rod, where the ratchet member has relatively large spaced tooth portions to engage the pawl member. Pumping the pusher bar mechanism causes the ratchet and pawl mechanism to urge the movable rod forward so that the jaws move closer together. A retaining mechanism comprising a pivotable clamp member having a central bore through which the movable rod member passes is provided, so that the edges of the central bore frictionally engage the movable rod member to allow it to move forwardly to close the gap between the jaws, but not rearwardly until the clamp member is pivoted to release the rod member. Once the initial, greater distance is approximated by the first advancing means, the second advancing means, which comprises a second pawl member positioned on the pusher bar mechanism which engages a second ratchet means having smaller teeth than the first ratchet means, is activated to incrementally advance the cartridge jaw towards the anvil jaw. After the staples or fasteners are fired, the jaws may be returned to their initial position by pivoting the pusher bar mechanism upwardly to disengage the pawl members from the ratchet members, so that a spring, biased in the rearward or handle direction, returns the fastening apparatus to its at rest position.

In a second embodiment, a pusher bar mechanism is provided at the distal end, or the handle end, of the surgical fastener applying apparatus. A ratchet and pawl mechanism is provided interiorly within the housing of the device, and is cooperatively engaged with the pusher bar mechanism. The pusher bar mechanism is linearly actuable so that the pusher bar mechanism may be pushed distally into the housing of the device by the thumb of the surgeon using the device. This initial distal thrust moves the cartridge jaw member towards the stationary anvil jaw member to substantially close the gap between the two jaw members to position and grip the tissue to be stapled or fastened therebetween. Once the initial push motion is completed, the pusher bar mechanism is pivotably actuated through a series of downwardly directed thrusts to "pump" the pusher bar mechanism. This pumping motion actuates the second advancing means which comprises the pawl mechanisms attached to the pusher bar mechanism, which engage a ratchet member fixedly positioned within the interior of the housing of the apparatus. The ratchet and pawl apparatus provides for incremental moving of the jaw assembly to provide a fine adjustment of the gap between the jaws. After firing the staples or fasteners into the tissue, the jaws may be returned to their rest position by pivoting the pusher bar mechanism upwardly to disengage the ratchet and pawl mechanism. A spring, biased in the proximal direction, returns the advancing means and the jaw mechanism to its original position.

In a third embodiment of the present invention, a push rod mechanism is provided where the rod member extends from the distal end of the device through the housing and is connected to the fastener driver and cartridge frame through a universal joint. The pusher rod mechanism comprises the advancing means which includes a first linear advancing means and a second rotatable advancing means. The rod member passes through the central bore of a pivotable clamp member which engages and holds the rod member along its path of travel to provide for a controlled adjustment of the spacing between the cartridge jaw and the anvil jaw. The pusher rod mechanism is thumb actuable by a surgeon to advance the rod through the clamp member to linearly advance the cartridge jaw towards the anvil jaw. The rod member is provided with a screw-threaded portion which engages the clamp member after the initial approximation. The jaws may be further incrementally approximated by rotating the pusher rod mechanism to advance the rod through the screw threads which engage the clamp member. This provides for fine adjustment of the spacing between the jaws. After the fasteners are fired through the tissue, the mechanism may be released by pivoting the clamp member to release the screw threads and consequently the rod member to return the rod member to its original position.

Preferably, a coupling mechanism is provided which couples the fastener driving means to the trigger mechanism to allow for driving of the staples or fasteners when the proper distance between the jaw members is set. As the approximating mechanism is actuated to move the cartridge frame, the cartridge and the fastener driving means forwardly, a coupling arm, which is connected at one end to the trigger mechanism, slides along a beating surface on the driving means until the approximating mechanism is fully deployed. At this point, a camming edge of the coupling arm engages a notch in the beating surface of the driving means to couple the trigger mechanism to the driving means. At this point, the proper distance between the jaw members is set and the fastener means may be driven into the tissue.

After the fastening means have been driven into the tissue, the releasable retaining mechanism may be disengaged so that the jaw members may be returned to their original position whereby the fastening device may be removed from the surgical site. In a first embodiment, the push bar mechanism is pivoted to disengage the retaining means directly. In a second embodiment, the push bar mechanism is pivotable to move a second rod member which serves as a release lever to disengage the reining means. In a third embodiment, a release knob or bar is provided which extends through the housing of the fastening apparatus and which may be pivoted to release the retaining means.

BRIEF DESCRIPTION OF THE DRAWINGS

The foregoing features of the present invention will become more readily apparent and may be understood by referring to the following detailed description of an illustrative embodiment of the surgical fastening instrument and its novel adjustable closure mechanism, taken in conjunction with the accompanying drawings, in which:

FIGS. 5a and 5b illustrate a side plan view and a top plan view, respectively, of the pusher bar mechanism of the adjustable closure mechanism of FIG. 2;

DETAILED DESCRIPTION OF THE PREFERRED EMBODIMENTS

Figure 1:
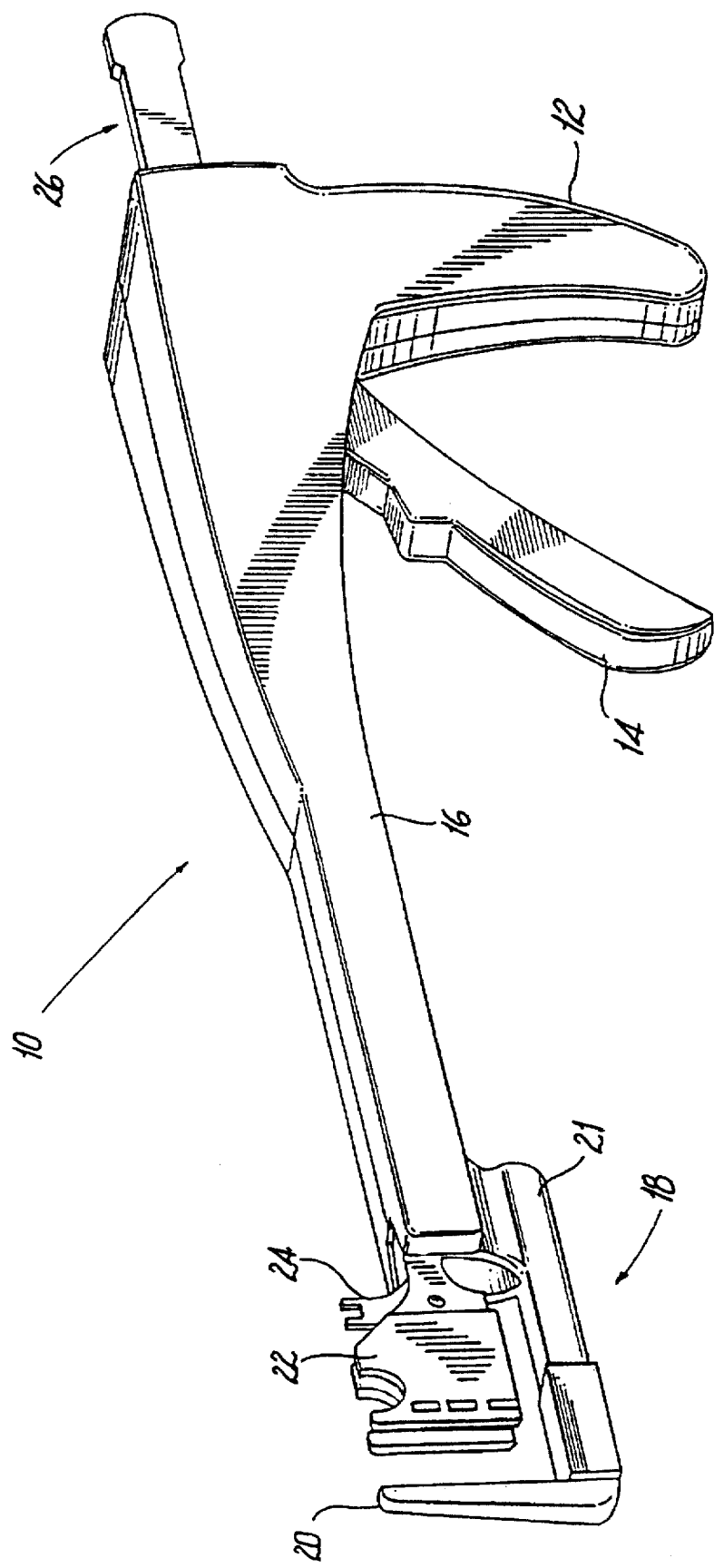
FIG. 1 illustrates a perspective view of a surgical fastening instrument employing the adjustable closure mechanism of the present invention.

Referring now in specific detail to the drawings, in which like reference numerals identify similar or identical elements throughout the several views, FIG. 1 shows a surgical fastening instrument 10 which employs the adjustable closure mechanism of the present invention. Fastening instrument 10 is provided with a stationary handle 12 and an actuating handle 14 which together comprise the trigger mechanism of instrument 10. An elongated body portion 16 is provided which terminates in a distal jaw mechanism 18 which includes an anvil jaw 20 and a cartridge jaw 22. A fastening cartridge (not shown) is positioned within cartridge jaw 22 for driving staples or fasteners through tissue against an anvil surface or into fastener retainers positioned on anvil jaw 20. At the handle end of instrument 10 is provided advancing mechanism 26 for advancing the cartridge jaw 22 towards anvil jaw 20.

Figure 2:
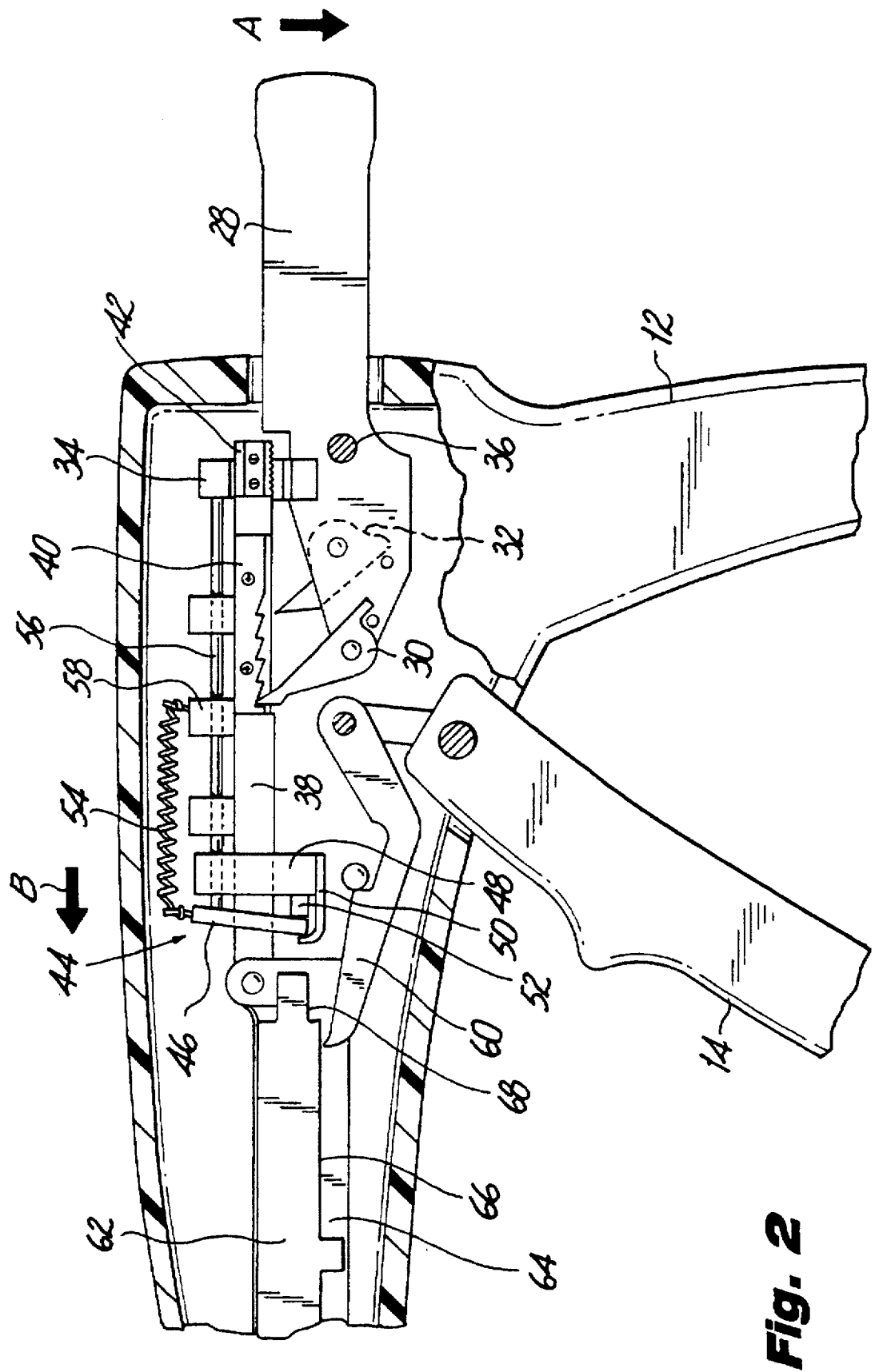
FIG. 2 illustrates a partial enlarged side cross sectional plan view of the handle end of a surgical instrument employing a first embodiment of the adjustable closure mechanism of the present invention in which the instrument is at an at rest condition.

As seen in FIG. 2, the advancing mechanism according to a first embodiment of the present includes a pusher bar mechanism 28 pivotably secured to the instrument at pivot point 36. The includes advancing mechanism 26 further includes first and second advancing mechanisms which approximate the spacing between cartridge jaw 22 and anvil jaw 20. The first advancing mechanism comprises the combination of first advancing pawl 30 and first advancing ratchet 40 which is secured to movable rod member 38. The second advancing means comprises a second advancing pawl 32 and a second advancing ratchet 42, where second advancing ratchet 42 is also disposed on movable rod 38. Pusher bar mechanism 28 is shown in detail in FIGS. 5a and 5b, and it can be seen that pawl members 30 and 32 are spring biased through the provision of spring members 29 and 33, respectively. Spring member 29 biases pawl member 30 by abutting against post member 31a as shown; spring member 33 biases pawl member 32 by abutting its respective post member 31b. A release block 34 is provided on pusher bar mechanism 28, whose function will be discussed below. Movable rod or connector member 38 passes through a retaining mechanism 44, and is secured to fastener driver 62 and cartridge frame 64 to advance these elements in a distal direction to approximate the distance between cartridge jaw 22 and anvil jaw 20. Retaining mechanism 44 is shown in detail in FIGS. 16a and 16b, as well as FIGS. 17a and 17b. Retaining mechanism 44 is biased into the engaged position by spring member 54, and may be moved to a disengaged position by release rod 56 which is slidably mounted in support blocks 58.

Ratchet 40 and pawl member 30 comprise the first advancing mechanism which approximates the distance between the jaw members an initial distance towards each other. The second advancing mechanism comprises ratchet 42 and pawl member 32 which advance the jaw members a second distance subsequent to approximation by the first advancing mechanism. As can be seen in the drawings, the teeth of ratchet 40 are much larger than the teeth of ratchet 42, and thus provide for greater movement of the jaws than the smaller teeth of ratchet 42.

Figure 16A:
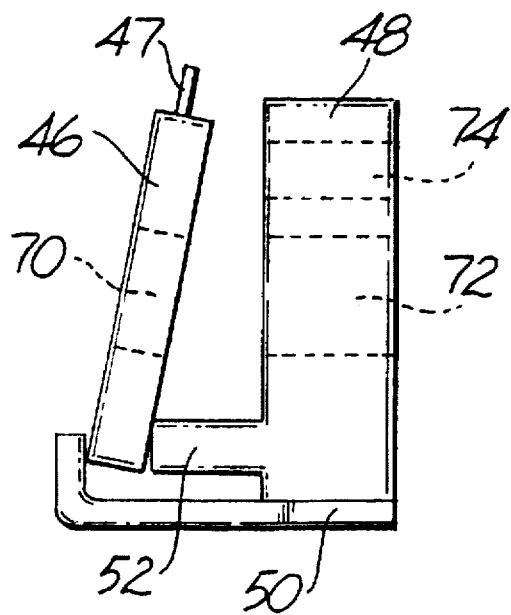
FIGS. 16a and 16b illustrate a side plan view and a front plan view, respectively, of a first embodiment of the retaining means of the adjustable closure mechanism of the present invention.
Figure 16B:
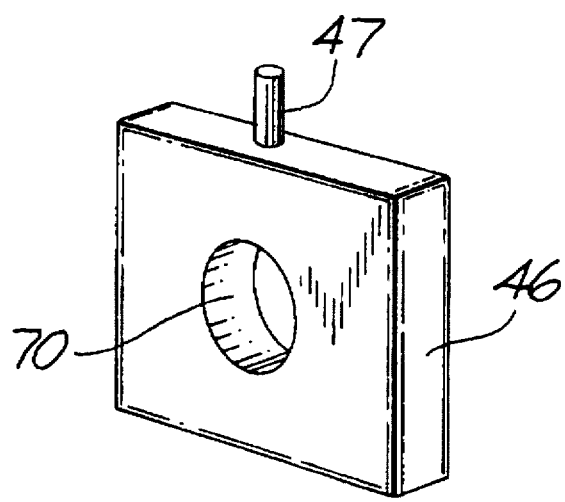

Retaining mechanism 44 comprises a clamp member 46 which is pivotably mounted on a carriage member 50 and is biased into the engaged position by biasing spring 54. As best seen in FIG. 16a and 16b, a block member 48 is provided having a shoulder portion 52 which provides a pivot point for clamp member 46. Clamp member 46 may include a spring post 47 as shown which engages biasing spring 54. Clamp member 46 further includes a central bore 70 through which movable rod 38 passes. In alignment with central bore 70 is a central bore 72 of block member 48 through which movable rod 38 also passes. A release bore 74 is also provided in block member 48 to allow release rod 56 to pass through and contact the upper portion of clamp member 46.

Figure 17A:
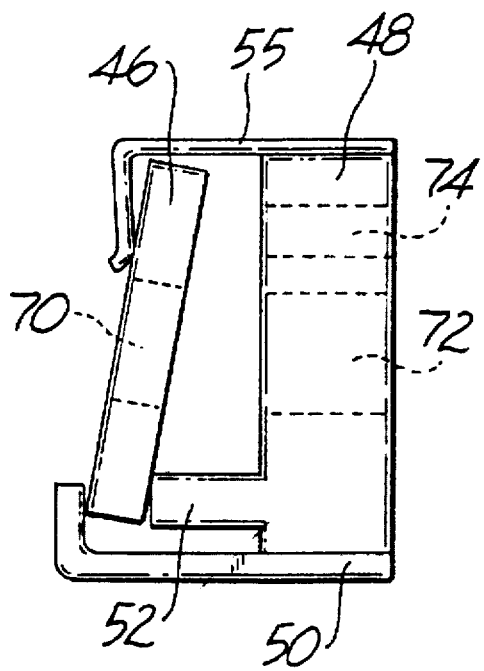
FIGS. 17a and 17b illustrate a side plan view and a front perspective view, respectively, of a second embodiment of the retaining means of the adjustable closure mechanism of the present invention.
Figure 17B:
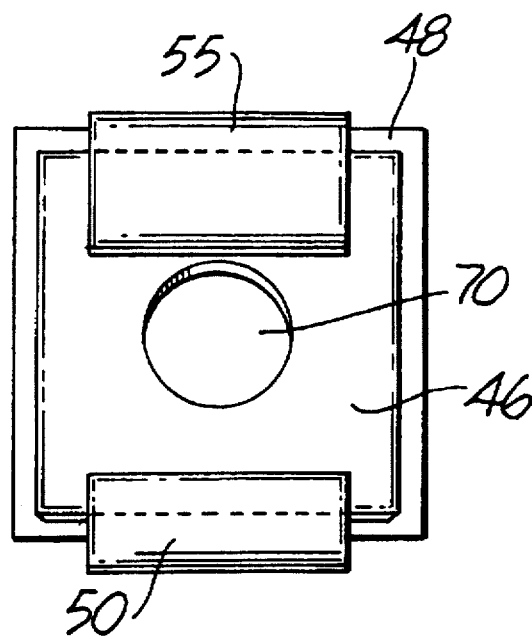

FIGS. 17a and 17b illustrate an alternate embodiment of retaining mechanism 44. The embodiment of FIG. 17a is identical to the embodiment of 16a except for the provision of a leaf spring 55 which provides the biasing force on clamp member 46 instead of biasing spring 54.

The operation of the adjustable closure mechanism of FIG. 2 will now be described. After the tissue to which the surgical fasteners are to be applied is positioned between cartridge jaw 22 and anvil jaw 20, cartridge jaw 22 is advanced distally to grip the tissue therebetween by activating advancement mechanism 26. Pusher bar mechanism 28 is pivotably actuated by pumping pusher bar mechanism 28 repeatedly in the direction of arrow A. The pusher bar mechanism 28 is biased to return to a rest position in substantial alignment with the longitudinal axis by a biasing means 29. This motion causes pawl member 30 to engage ratchet 40 to urge movable rod 38 in the direction of arrow B. Movable rod 38 is prevented from moving rearwardly by retaining mechanism 44. As pusher bar mechanism 28 is pumped in the direction of arrow A, pawl member 30 engages successive teeth of ratchet 40 to move rod member 38 forwardly. Moving movable rod 38 forwardly causes fastener driver 62 and cartridge frame 64 to move forwardly as cartridge jaw 22 moves towards anvil jaw 20 to grip the tissue therebetween. When pawl member 30 is engaged in the last tooth of ratchet 40 at the proximal end of ratchet 40, pawl member 32 engages the first tooth at the distal end of ratchet 42. Ratchet 42 and pawl member 32 provide for incremental adjustment of the distance between cartridge jaw 22 and anvil jaw 20 and moves movable rod 38 over small distances compared to the distance traversed through the cooperation between pawl member 30 and ratchet means 40.

Figure 3:
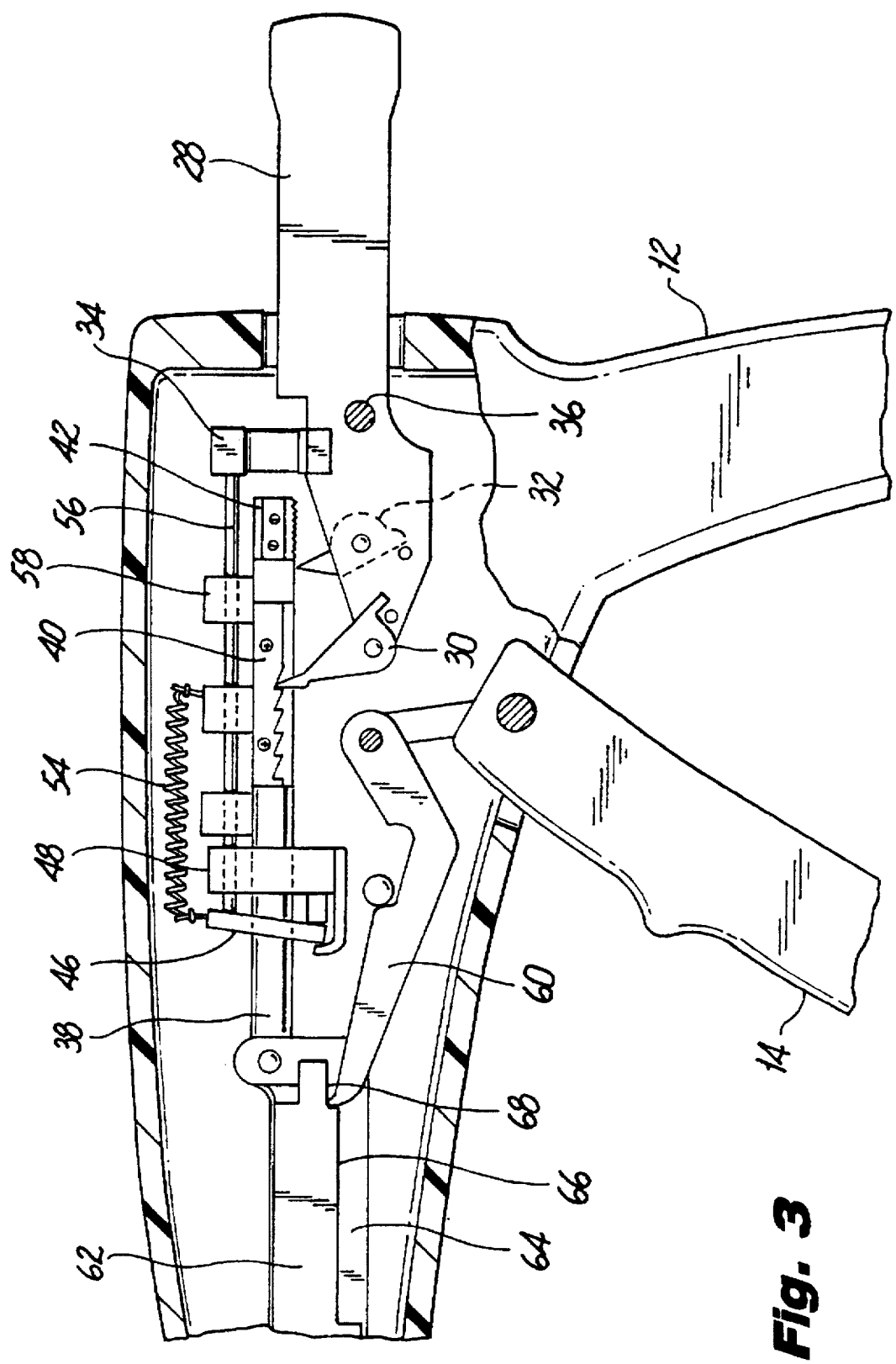
FIG. 3 illustrates a partial enlarged side cross sectional plan view of the device of FIG. 2 in which the adjustable closure mechanism of the present invention is fully deployed so that the device is in the fully loaded condition.
Figure 15A:
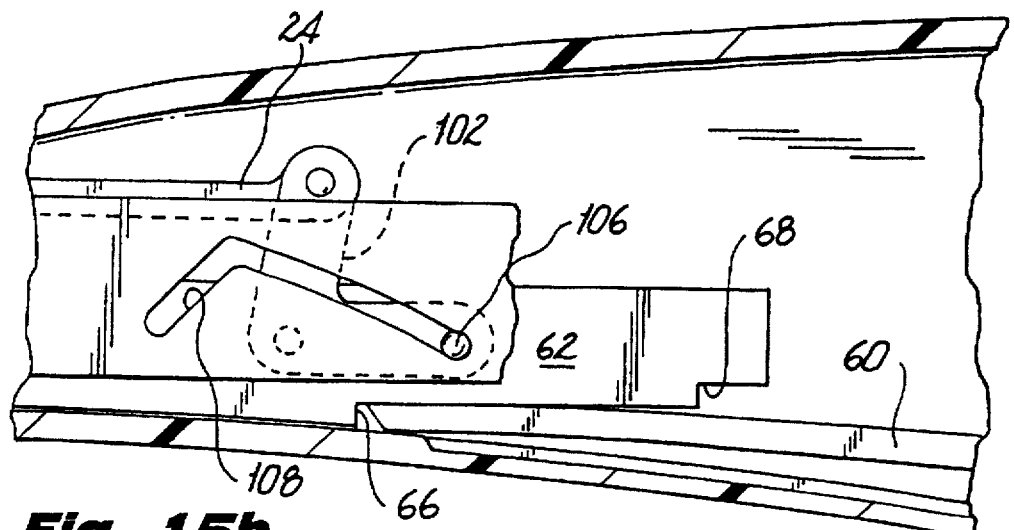
FIGS. 15a through 15c illustrate the coupling mechanism according to the present invention for coupling the trigger mechanism to the fastener driving mechanism used in conjunction with the adjustable closure mechanism of the present invention.
Figure 15B:
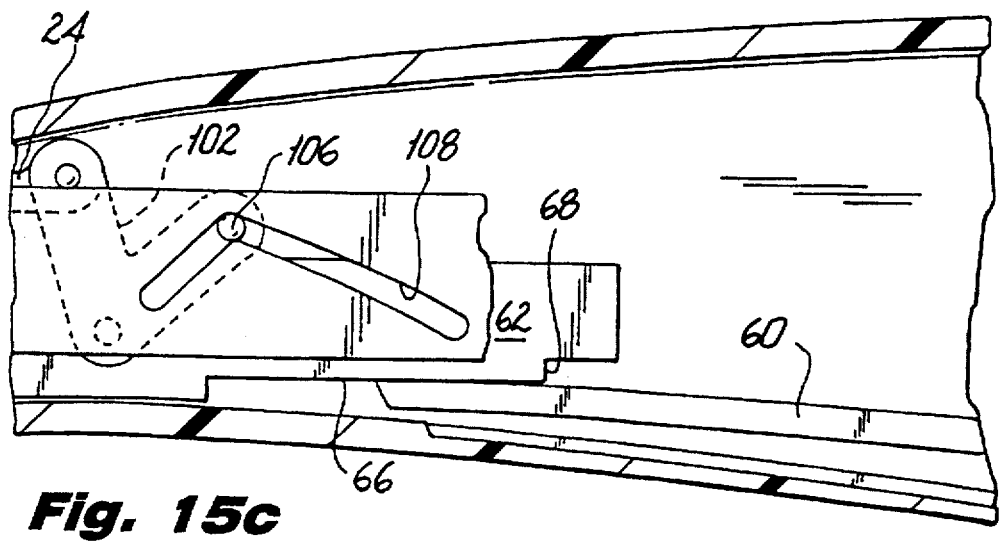
Figure 15C:
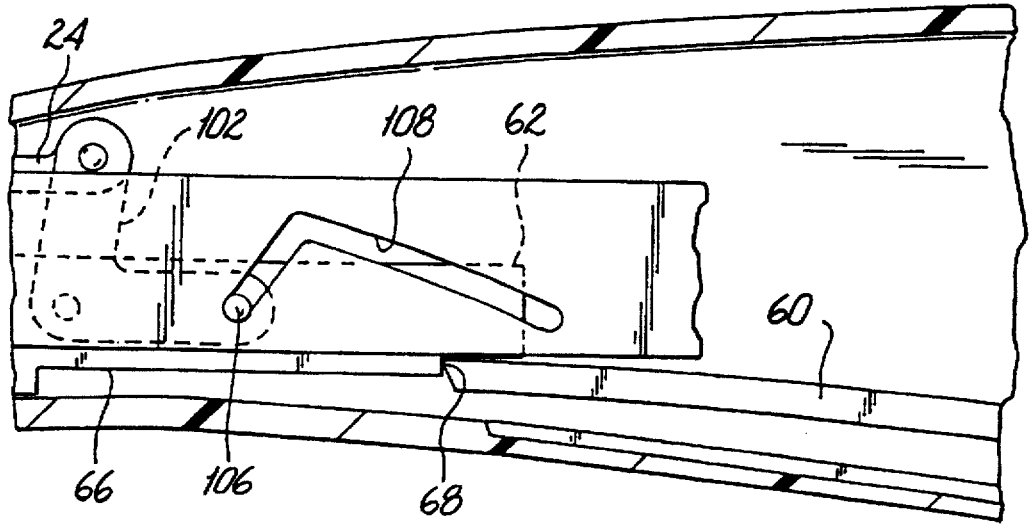

As movable rod 38 urges fastener driver 62 and cartridge frame 64 forwardly, coupling arm 60, as best seen in FIGS. 15a through 15c, slides along bearing surface 66 of fastener driver 62 until the jaws are approximated at the desired distance, when coupling arm 60 is engaged in notch 68 to permit driving of the fasteners into the tissue. This position is clearly seen in FIG. 3. At this point, actuating handle 14 may be moved towards stationary handle 12 to fire the fasteners into the tissue.

Figure 4:
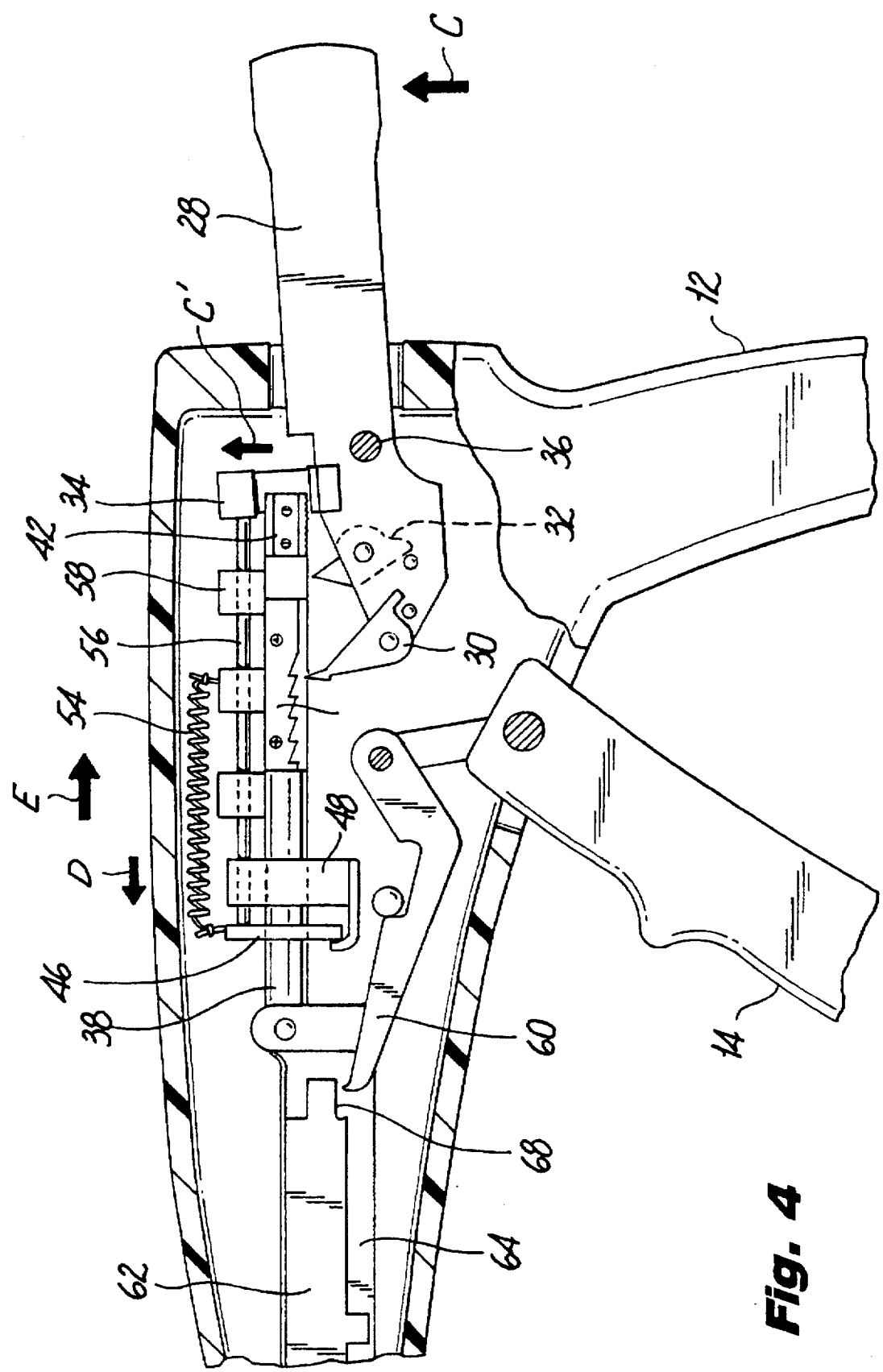
FIG. 4 illustrates a partial enlarged side cross sectional plan view of the handle end of the surgical instrument of FIG. 2 in which the release mechanism has been activated to disengage the retaining means and the adjustable closure mechanism.

After the fasteners are driven into the tissue, the advancing mechanism, and the cartridge jaw, may be returned to the position shown in FIG. 2 by releasing the retaining mechanism 44. As best seen in FIG. 4, this is accomplished by pivoting the pusher bar mechanism 28 in the direction of arrow C so that release block 34 is moved in the direction of the arrow C'. Release block 34 engages the rear end of release rod 56 which urges release rod 56 forwardly through support blocks 58 and against the upper portion of clamp member 46. Clamp member 46 is moved in the direction of arrow D to disengage the edges of central bore 70 from movable rod 38. Release block 34 also lifts support blocks 58 to lift ratchet mechanisms 40 and 42 away from pawl members 30 and 32, respectively, to allow movable rod 38 to move rearwardly in the direction of arrow E to return the instrument to the at rest position shown in FIG. 2.

Figure 6:
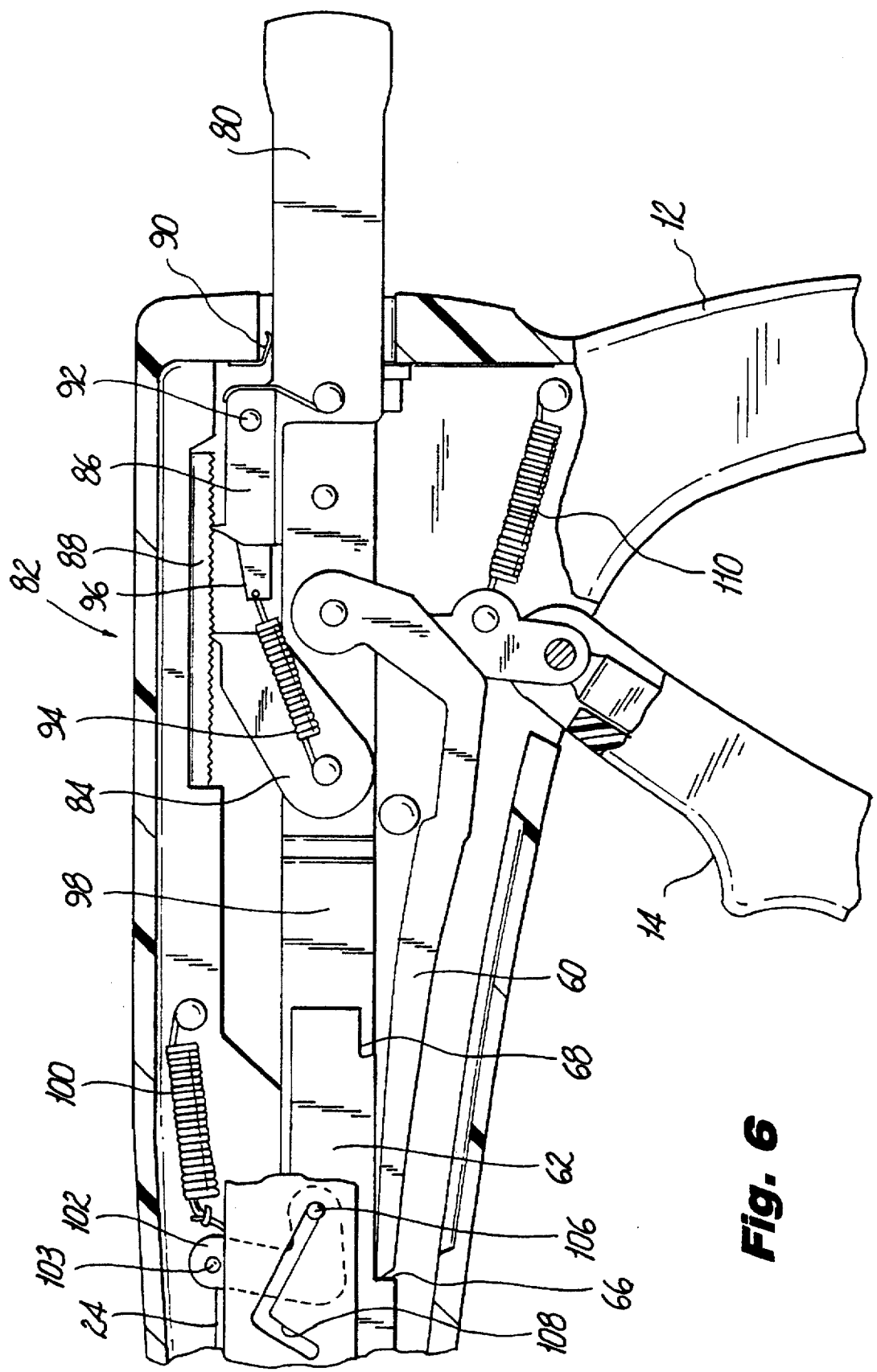
FIG. 6 illustrates a partial enlarged side cross sectional plan view of the handle end of a surgical fastening instrument in a rest condition employing a second embodiment of the adjustable closure mechanism of the present invention.

FIGS. 6–11 illustrate an alternate embodiment of the adjustable closure mechanism of the present invention. A pusher bar mechanism 80 is provided at the handle end of the instrument for operating the advancing mechanism 82 to approximate the distance between cartridge jaw 22 and anvil jaw 20. Similar to advancing mechanism 28 above, advancing mechanism 82 as shown in FIG. 6 comprises a first advancing means for approximating the cartridge jaw 22 in relation to anvil jaw 20 a large distance, and also includes a second advancing means for incrementally advancing cartridge jaw 22 towards anvil jaw 20 subsequent to the initial movement.

Pusher bar mechanism 80 is secured to the advancing mechanism 82 and is further secured to cartridge frame advancing rod 98 for advancing cartridge jaw 22 towards anvil jaw 20. Fastener driver 62 is secured to cartridge frame advancing rod 98 through a linkage arrangement which includes an L-shaped driving link 102, and a driving pin 106 whose function will be described below.

Figure 7:
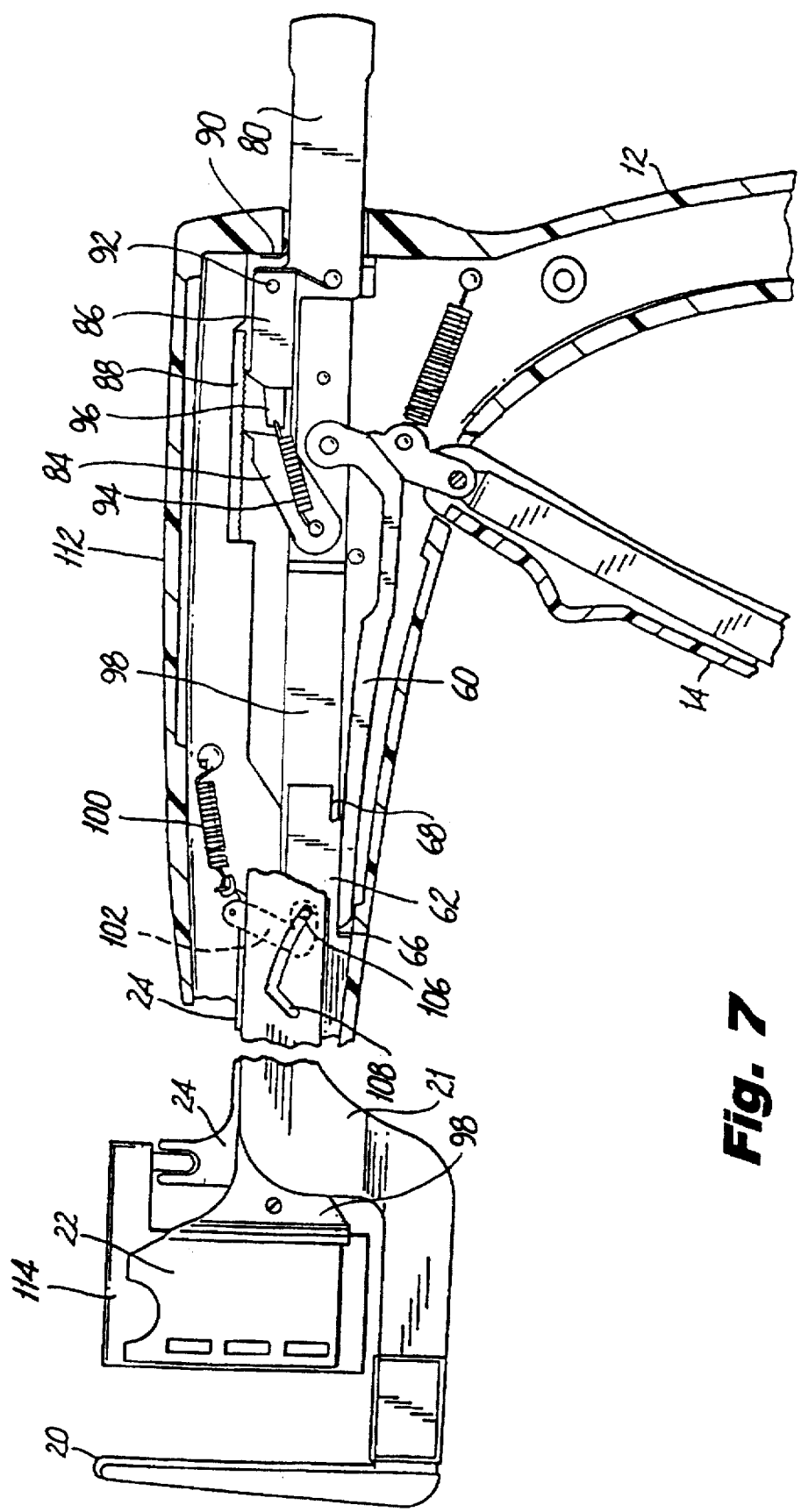
FIG. 7 illustrates a side cross sectional plan view of a surgical fastening instrument employing the adjustable closure mechanism of FIG. 6 in which the instrument is in an at rest condition.
Figure 8:
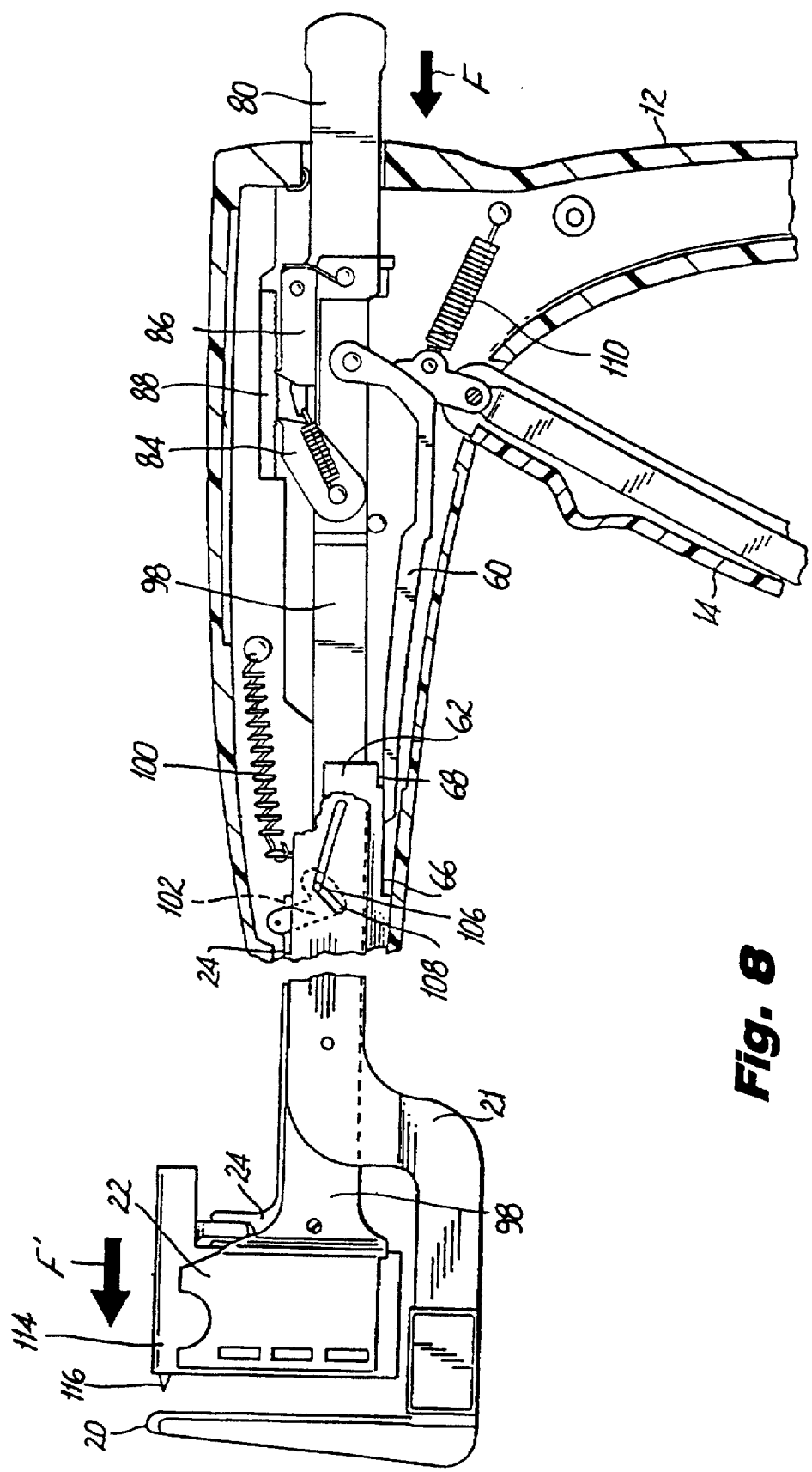
FIG. 8 illustrates the device of FIG. 6 in which the adjustable closure mechanism is activated and the jaw mechanism is partially closed.

The operation of advancing mechanism 82 will now be described in reference to drawing FIGS. 7–10. As best seen in FIG. 7, the instrument is in an at rest position where cartridge jaw 22 and cartridge 114, which includes fasteners as is well known in the art, are positioned away from anvil jaw 20. The cartridge 114 includes fasteners, as is well known in the art. Driving pin 106 is positioned at the proximal end of frame track 108 and is secured to L-shaped driving link 102 as shown. A top end of link 102 is secured to alignment pin advancement means 24 by pin 103. Coupling arm 60 is positioned on bearing surface 66 of fastener driver 62. Once tissue to be fastened or stapled is positioned between the cartridge jaw 22 and anvil jaw 20, pusher bar mechanism 80 is urged forwardly in the direction of arrow F as best seen in FIG. 8. Advancement of pusher bar mechanism 80 in the direction of arrow F comprises the first advancing means of advancing mechanism 82. The advancing pawl means 84 and advancing pawl means 86 slide over ratchet means 88 due to the forward movement of pusher bar mechanism 80. When resistance to further forward movement of the cartridge 114 and cartridge jaw 22, which are moved in a direction of arrow F, is felt by the surgeon, movement of the pusher bar mechanism 80 in the direction of arrow F is ceased. As can be clearly seen in FIG. 8, movement of pusher bar mechanism 80 causes movement of fastener driver 62 which causes coupling arm 60 to slide along bearing surface 66 as shown. Driving pin 106 travels along frame track 108 to the point shown in FIG. 8, whereby the driving link 30 pivots as shown and urges the alignment pin advancement means 24 (formed as a slide bar) forwardly, which in turn causes alignment pin 116 to be moved through cartridge 114 towards an alignment hole in anvil jaw 20 (not shown). Alignment pin 116 cooperates with the alignment hole in anvil jaw 20 to provide for proper alignment of the fasteners with the anvil surface on anvil jaw 20. Anvil jaw 20 may also include means for holding a plurality of retainers which engage fasteners loaded in cartridge 114. Biasing spring 100 begins to extend as shown in FIG. 8.

Figure 9:
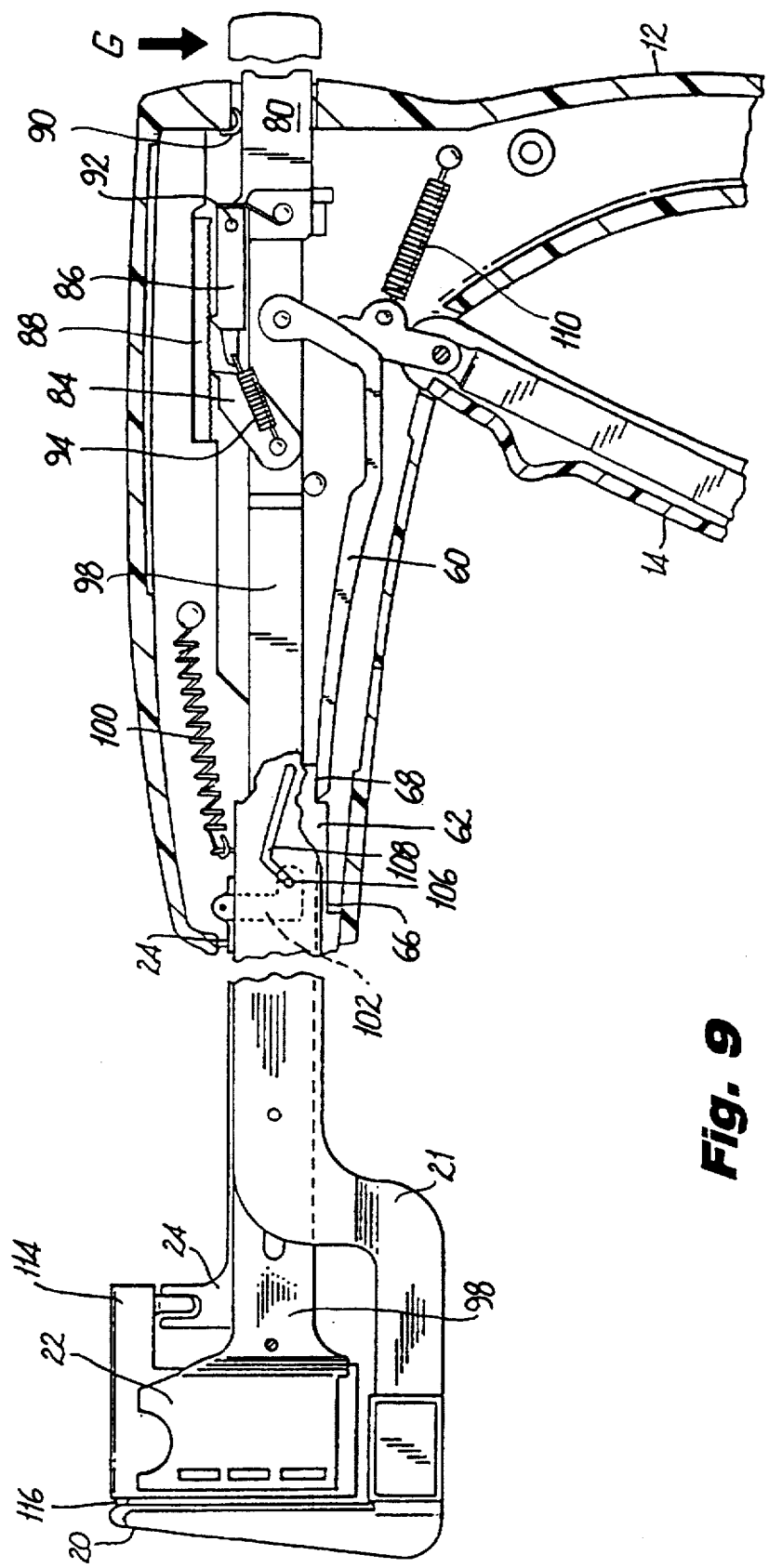
FIG. 9 illustrates a device of FIG. 6 in which the adjustable closure mechanism of the present invention is fully deployed so that the device is in the fully loaded condition.

Once resistance due to the tissue positioned between the jaw members has been encountered, cartridge jaw 22 may be further advanced incrementally by using the second advancement means to provide for fine adjustment of the spacing between the jaw members. In order to accomplish this, as best seen in FIG. 9 (with reference to FIG. 6), pusher bar mechanism 80 is reciprocatingly pivoted in the direction of arrow G to urge cartridge frame advancing rod 98 forwardly by using advancing pawl means 84 and advancing pawl means 86, which engage ratchet means 88. Pawl means 84 and 86 remain in engagement with ratchet means 88 through the provision of pawl spring 94.

Figure 11:
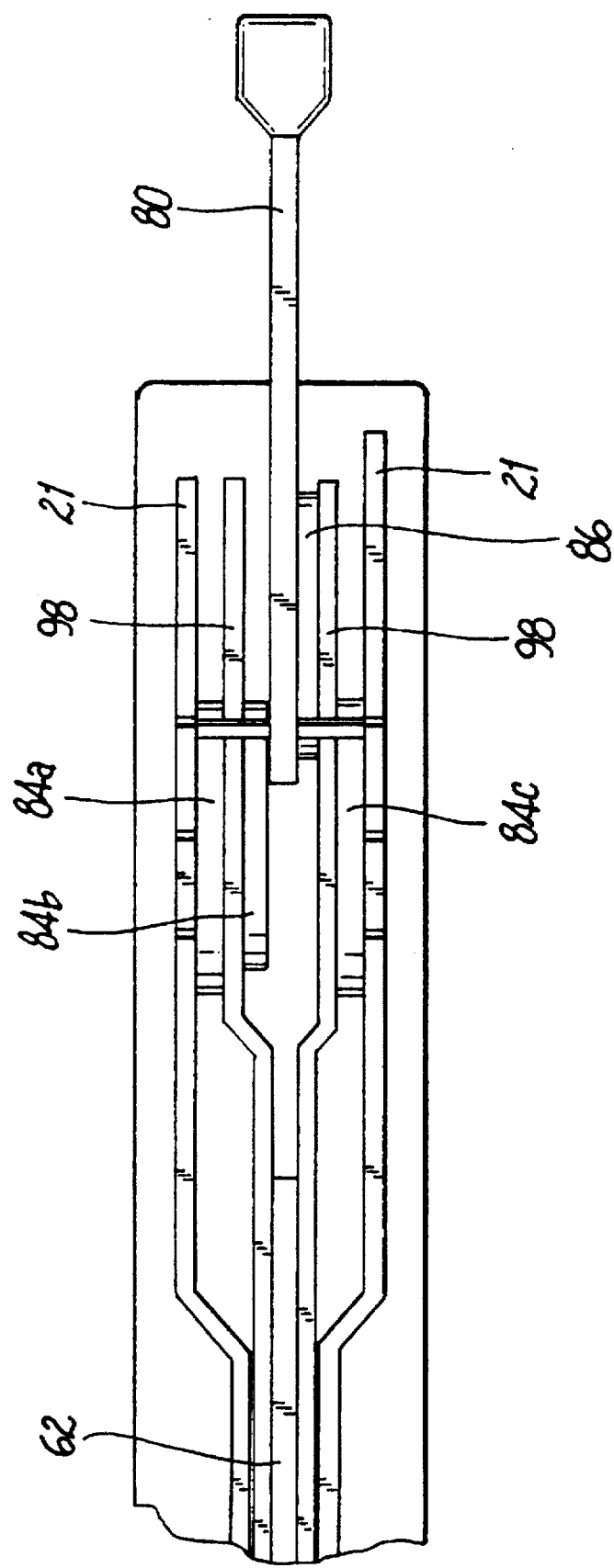
FIG. 11 illustrates a bottom plan view of the adjustable closure mechanism of FIG. 6.

Referring to FIG. 11, which is a view from beneath the mechanism of FIG. 7, it can be seen that advancing pawl means 84 comprises a plurality of pawl members, in this instance three, namely pawl members 84a, 84b and 84c. Pawl members 84a, 84b and 84c are slightly offset from each other, and successively and incrementally move cartridge frame advancing rod 98 once each prior to movement of advancing pawl member 86. Preferably, each pawl member 84a, 84b and 84c move rod 98 0.033 inches so that when each pawl member 84a, 84b and 84c has moved successively, advancing pawl member 86 then moves 0.10 inches. Pawl member 86 serves as a retaining mechanism to prevent rod member 98 from moving rearwardly due to biasing spring 100 while each pawl member 84a through 84c are moving. Continued pumping of push bar mechanism 80 in the direction of arrow G will incrementally move cartridge jaw 22 and cartridge 114 towards anvil jaw 20.

As the distance between the jaw members is set to a desired distance, driving pin 106 moves to the distal end of frame track 108 so that drive link 102 assumes a substantially vertical position as shown in FIG. 9. This draws alignment pin advancing means 24 slightly rearwardly so that alignment pin 116 engages the hole in anvil jaw 20 but does not extend beyond the jaw as shown. Cartridge frame advancing rod 98, cartridge jaw 22, and cartridge 114 are now in position for firing. At this point, due to the movement of driving pin 106, fastener driver 62 has moved into position to fire the fasteners into the tissue. This can be seen by the engagement of coupling arm 60 in notch 68 of fastener driver 62. Coupling arm 60 has slid off bearing surface 66 and into notch 68 so that the fasteners may be fired.

Figure 10:
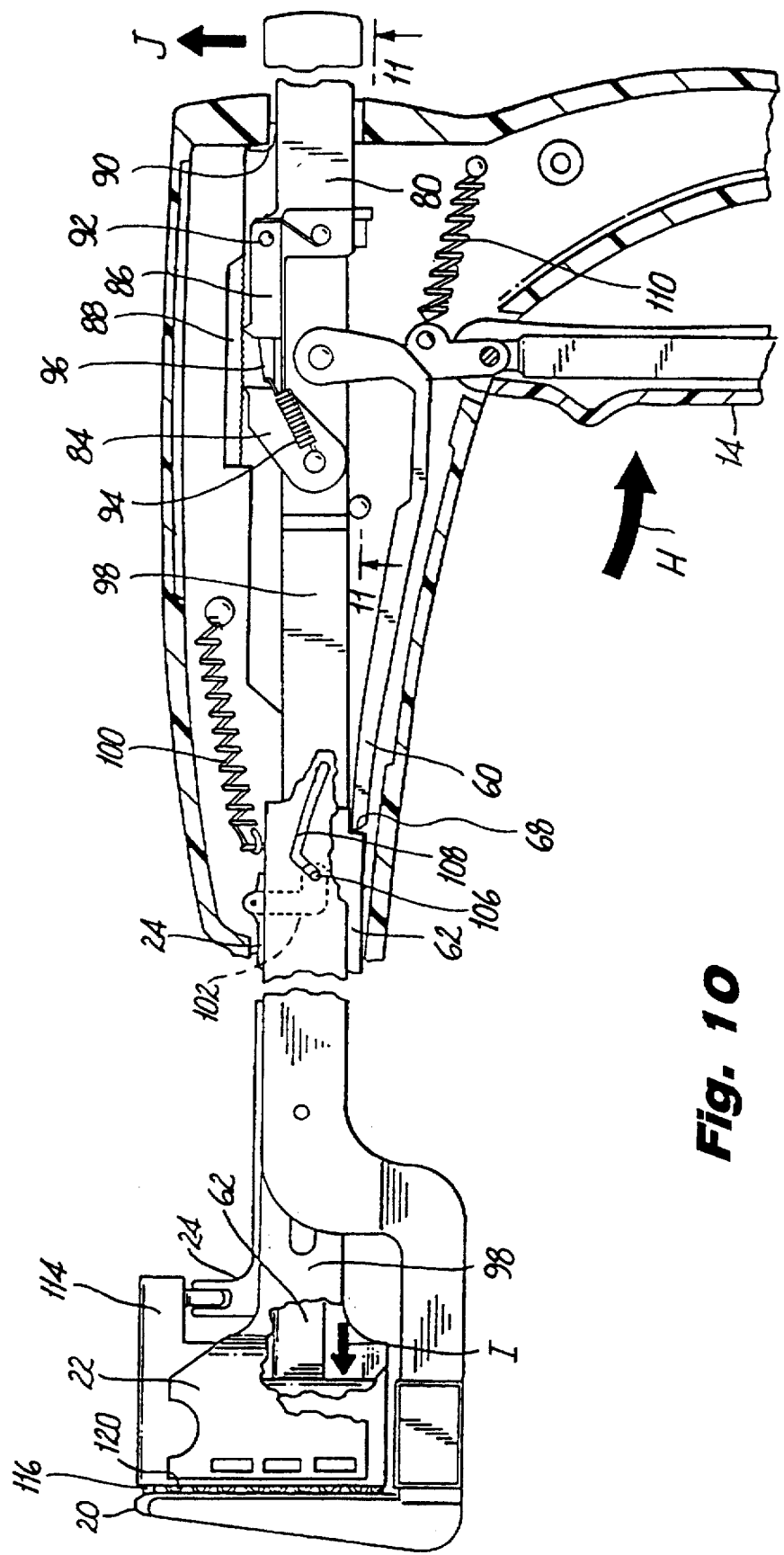
FIG. 10 illustrates the device of FIG. 6 in which the adjustable closure mechanism of the present invention is fully deployed and the trigger mechanism of the device has been actuated so that the fastening means have been driven from the cartridge.

Fasteners 120 are driven into the tissue by moving actuating handle 14 in the direction of arrow H as shown in FIG. 10. Coupling arm 60 moves fastener driver 62 forwardly in the direction of arrow I to drive the fasteners 120 into the tissue. After firing, actuating handle 14 is returned to its at rest position by biasing spring 110. In order to release the jaws to remove the instrument from the surgical site, pusher bar mechanism 80 is pivoted upwardly in the direction of arrow J against biasing spring 90 about pivot member 92 which pivots pawl means 86 away from ratchet means 88. Release extension 96, in conjunction with pawl spring 94 pivots pawl means 84a through 84c away from ratchet means 88 to release the entire mechanism and return the instrument to the position shown in FIG. 7.

Figure 12:
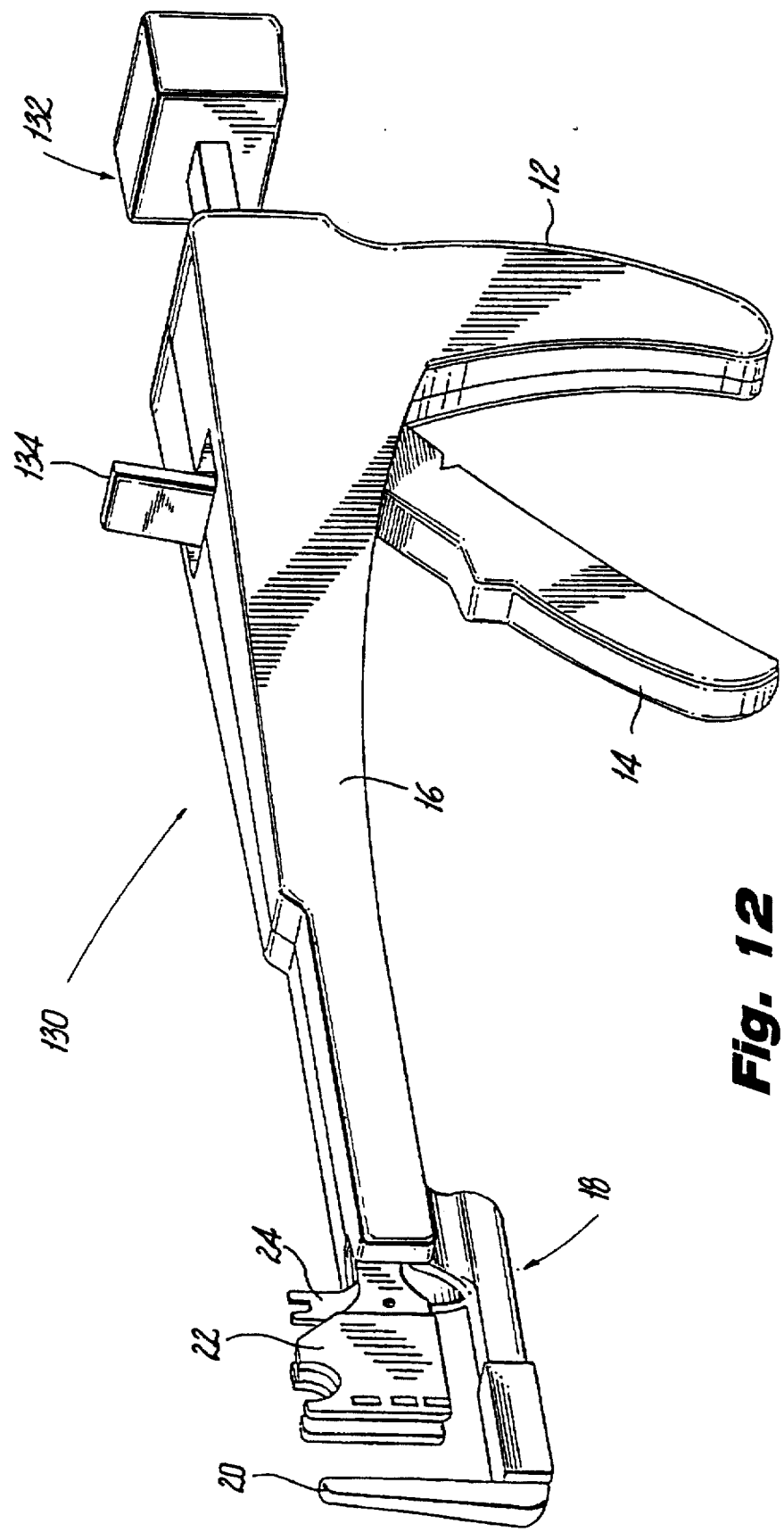
FIG. 12 illustrates a perspective view of a surgical fastening instrument employing a third embodiment of the adjustable closure mechanism of the present invention.
Figure 13:
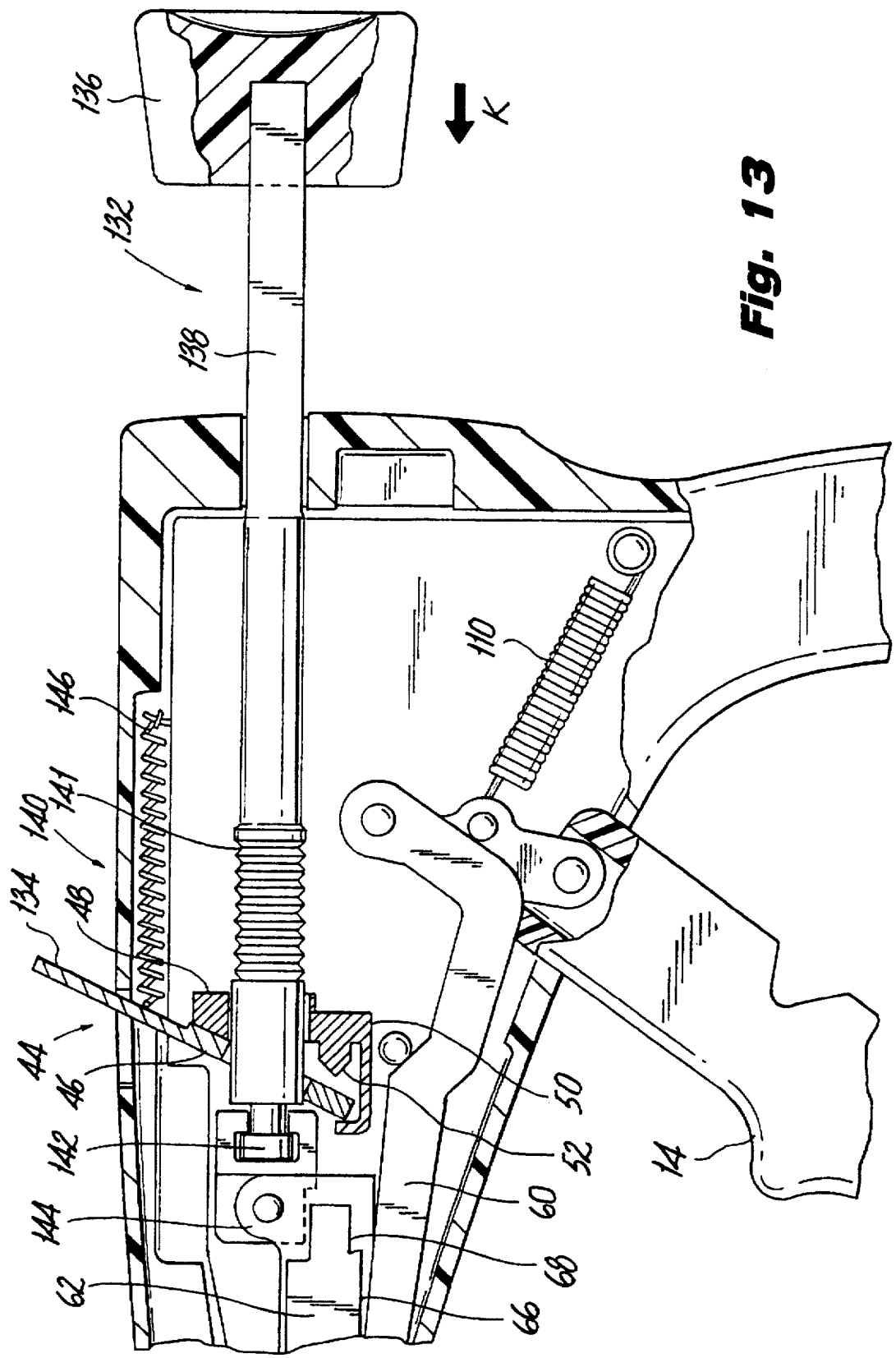
FIG. 13 illustrates a partial enlarged side cross sectional plan view of the handle end of the surgical fastening instrument of FIG. 12 employing the third embodiment of the adjustable closure mechanism of the present invention in which the instrument is in an at rest condition.
Figure 14:
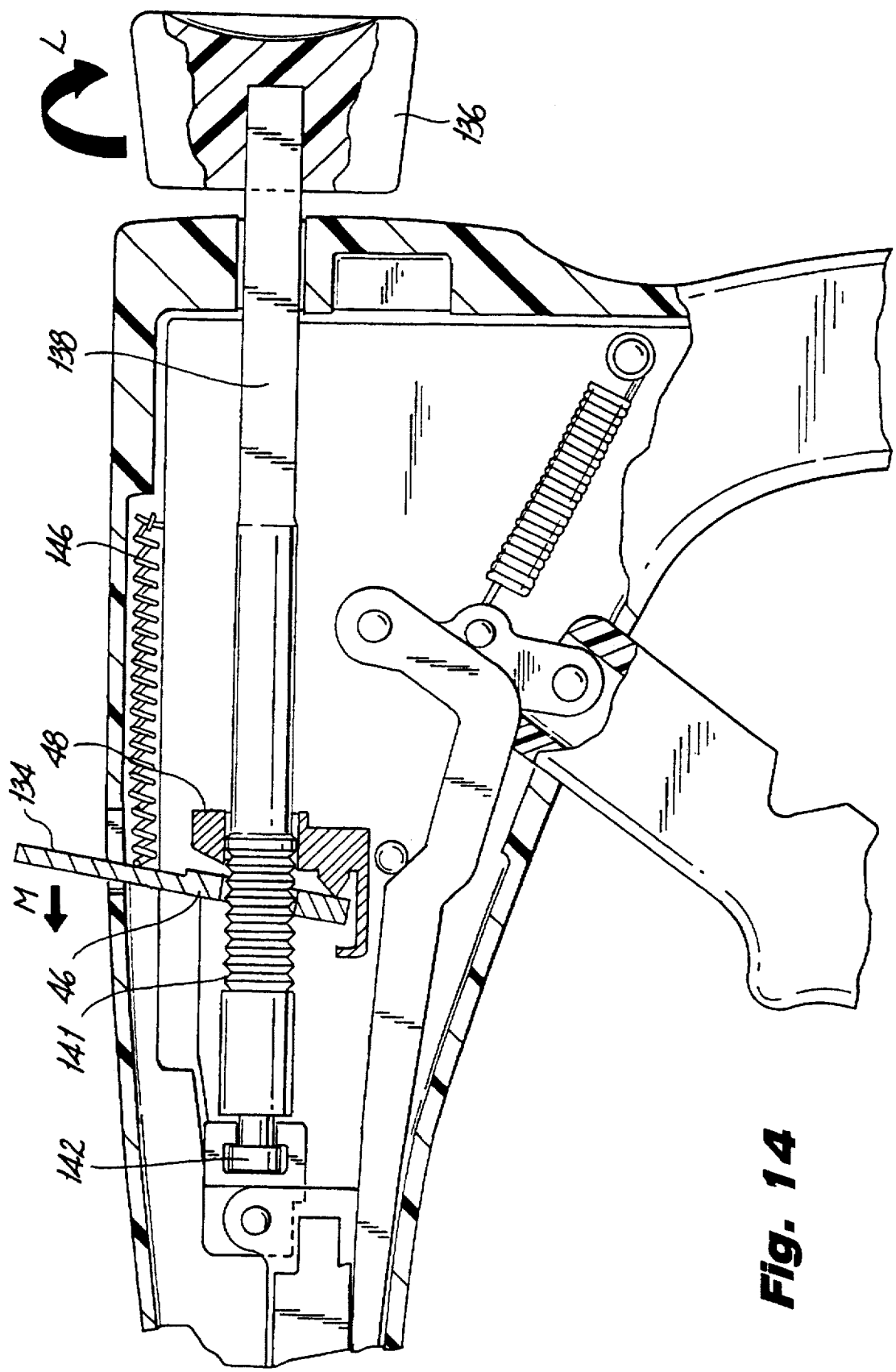
FIG. 14 illustrates a partial enlarged side cross sectional plan view of the handle end of the surgical fastening instrument in which the third embodiment of the adjustable closure mechanism of the present invention is fully deployed so that the device is in the fully loaded condition.

FIGS. 12 through 14 illustrate a surgical fastening apparatus 130 employing a further embodiment of the advancing mechanism of the present invention. Device 130 includes actuating handle 14, stationary handle 12, and body portion 16 which terminates in a jaw mechanism 18 similar to that described above. Jaw mechanism 18 includes an anvil jaw 20, a movable cartridge jaw 22, and an alignment pin advancement means 24 similar to that described above. Instrument 130 further includes a first advancing mechanism 132 and a release knob or bar 134 for releasing a reining mechanism which will be described below.

Turning now to FIGS. 13 and 14, there is illustrated the retaining mechanism 44 which is similar to that described above. Retaining mechanism 44 includes a clamp member 46 to which release bar 134 is attached. Retaining mechanism 44 further includes block member 48 having shoulder 52, all of which are mounted to carriage 50 as described above and best shown in FIGS. 16a and 16b and 17a and 17b.

First advancing mechanism 132 comprises a pusher knob 136 for advancing an advancing rod or member 138 into the housing of instrument 130. In use, pusher knob 136 is urged forwardly in the direction of arrow K to move advancing rod 138 forwardly. Advancing rod 138 further includes second advancing mechanism 140, which comprises screw threads 141, whose function will be described below. Advancing rod 138 and screw threads 141 pass through central bore 70 of clamp member 46 and central bore 72 of block member 48 and terminate in universal joint 142 which is attached to cartridge frame 144 and fastener driver 62 whose functions are identical to that described above.

Turning now to FIG. 14, advancing rod 138 is moved forwardly until clamp member 46 engages screw threads 141. At this point, cartridge jaw 22 has been approximated a great distance towards anvil jaw 20 to grip tissue therebetween. Pusher knob 136 may then be rotated by the thumb of the surgeon in the direction of arrow L to further advance cartridge jaw 22 towards anvil jaw 20, since the rotational motion is for fine adjustment of the spacing over a small distance. Rotation of pusher knob 136 allows advancing rod 138 to further move forwardly through the cooperation of screw threads 141 with central bore 70 of clamp member 46. The rotational movement of rod 138 is translated into longitudinal movement through the provision of universal joint 142. After the jaws have been approximated to a desired distance, coupling arm 60 engages notch 68 of fastener driver 62 and actuating handle 14 may be moved towards stationary handle 12 to fire the fasteners into the tissue. The following firing of the fasteners, the entire mechanism may be released and returned to its at rest position by moving release bar 134 in the direction of arrow M to disengage screw threads 141 from central bore 70. Release bar 134 moves in the direction of arrow M against biasing spring 146 which maintains engagement of central bore 70 with rod member 138.

The adjustable closure mechanism of the present invention can also be used in other instruments to dose the distance between the movable jaw member and the stationary jaw member at the stapling or fastening end of the instrument or between two movable jaw members. That is, the jaw mechanism may be of the type wherein one jaw moves toward and away from the other; however, the present invention is also applicable for use with devices of alternative types, i.e., where both jaws move toward and away from each other. The surgical instrument may be of the type which applies metal staples or two-part fasteners of the bioabsorbable type.

The surgical stapling or fastening instrument employing the adjustable closure mechanism of the present invention is a device which may be operated with one hand to effect the closure motion of the jaw members of the instrument followed by activation of the trigger mechanism to fire the staples or fasteners into the tissue. The complex rotational or pivoting arrangement of the prior devices is eliminated, resulting in a lightweight and easy to handle instrument which is inexpensive to manufacture and easy to assemble.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical fasteners to body tissue comprising:

tissue gripping means for positioning and gripping tissue therebetween, said gripping means including a first jaw member and a second jaw member, said first jaw member having a plurality of fasteners positioned thereon; and an advancing mechanism operatively associated with said first jaw member for urging said first jaw member towards said second jaw member, said advancing mechanism including an advancing member being linearly movable for urging said first jaw member towards said second jaw member a predetermined distance and said advancing member further being rotatable for urging said first jaw member towards said second jaw member to grip said tissue therebetween.

2. An apparatus according to claim 1, further comprising releasable retaining means for retaining said advancing mechanism to selectively position said first jaw member in relation to said second jaw member.

3. An apparatus according to claim 2, wherein said actuator member comprises a rod member which extends from a housing of said apparatus.

4. An apparatus according to claim 3, wherein said advancing member further comprises screw threads integral to said rod member, said screw threads engaging said retaining means for incrementally advancing said first jaw member in relation to said second jaw member.

5. An apparatus according to claim 4, wherein linear movement of said advancing member advances said first jaw member towards said second jaw member a greater distance than rotatable movement of said advancing member.

6. An apparatus according to claim 4, wherein said retaining means comprises a pivotable clamp member having a central bore through which said advancing member passes, an edge of said central bore engaging said advancing member to retain said advancing member and selectively position said first jaw member in relation to said second jaw member.

7. An apparatus according to claim 1, wherein said advancing member is rotatable to urge said first jaw member towards said second jaw member subsequent to the linear movement of said advancing member.

8. An apparatus according to claim 1, further comprising means for driving said fasteners into said tissue, said driving means including means for operating said driving means.

9. An apparatus according to claim 8, further comprising means for coupling said driving means to said operating means, said driving means driving said fasteners only when said first jaw member is approximated a predetermined distance from said second jaw member.

10. An apparatus for applying surgical fasteners to body tissue, comprising:

first and second jaws, the first jaw having a plurality of fasteners positioned thereon;

a first advancing mechanism operably associated with the first jaw and being movable to advance the first jaw towards the second jaw a first predetermined distance;

a second advancing mechanism operably associated with the first jaw and being movable to advance the first jaw towards the second jaw a second predetermined distance subsequent to movement of the first jaw the first predetermined distance; and a fastener driver movably positioned in relation to the first jaw to eject the fasteners:

wherein the first and second advancing mechanisms have a common actuator member.

11. An apparatus according to claim 10 wherein the first and the second advancing mechanisms include a first ratchet and pawl mechanism and a second ratchet and pawl mechanism, respectively.

12. An apparatus according to claim 10, wherein the common actuator member includes a pusher bar operably connected to the first and second advancing mechanisms, the pusher bar having a proximal end extending from a proximal end of a housing of the apparatus.

13. An apparatus according to claim 12 wherein the pusher bar is pivotably connected to the housing of the apparatus, and the first and second advancing mechanisms include first and second ratchet and pawl mechanisms, respectively.

14. An apparatus according to claim 13 further including a movable rod operably connected to the first jaw, wherein the first and second ratchet and pawl mechanisms include a first ratchet member and first pawl member, and a second ratchet member and second pawl member, respectively, the first and second pawl members being connected to the pusher bar and the first and second ratchet members being connected to the movable rod.

15. An apparatus according to claim 14 wherein the second ratchet and pawl mechanism is configured to advance the first jaw towards the second jaw in smaller increments than the first ratchet and pawl mechanism.

16. An apparatus according to claim 10 wherein the first advancing mechanism includes an advancing rod movable linearly to advance the first jaw towards the second jaw, and the second advancing mechanism includes screw threads operatively associated with said advancing rod and being rotatable to advance the first jaw towards the second jaw.

17. An apparatus according to claim 16 wherein the first predetermined distance is greater than the second predetermined distance.

18. An apparatus for applying surgical fasteners to body tissue, comprising:
  first and second jaws, the first jaw having a plurality of fasteners positioned thereon;
  a first advancing mechanism operably connected to the first jaw and being linearly movable to advance the first jaw towards the second jaw a first predetermined distance;
  a second advancing mechanism operably connected to the first jaw and being rotatable to advance the first jaw towards the second jaw a second predetermined distance subsequent to movement of the first jaw the first predetermined distance; and
  a fastener driver movably positioned in relation to the first jaw to eject the fasteners.

19. An apparatus according to claim 18 wherein the first advancing mechanism includes a linearly slidable rod operably connected to the first jaw and the second advancing mechanism includes screw threads formed on the slidable rod.

20. An apparatus according to claim 19 further comprising a retaining mechanism positioned adjacent the slidable rod, at least a portion of the retaining mechanism being movable from a first position spaced from the slidable rod to a second position engaging the slidable rod to thereby selectively position the first jaw in relation to the second jaw.

21. An apparatus according to claim 20 wherein the retaining mechanism includes a pivotable clamp member having a central throughbore through which the slidable rod passes, an edge of the throughbore engaging the slidable rod in the second position of the retaining mechanism.

22. An apparatus according to claim 21 wherein the screw threads are positioned on the slidable rod to engage the clamp member after the first jaw has been advanced the first predetermined distance, to thereby facilitate rotatable incremental advancement of the first jaw towards the second jaw.

23. An apparatus according to claim 20 further including a release bar operably connected to the movable portion of the retaining mechanism, the release bar extending through a housing of the apparatus and being movable to move the movable portion of the retaining mechanism from the second position to the first position.

24. An apparatus for applying surgical fasteners to body tissue, comprising:
  first and second jaws, the first jaw having a plurality of fasteners positioned thereon;
  an advancing mechanism operably connected to the first jaw, at least a portion of the advancing mechanism being pivotable about an axis transverse to a longitudinal axis of the apparatus and being reciprocable to incrementally advance the first jaw towards the second jaw; and
  a fastener driver movably positioned in relation to the first jaw to effect ejection of the fasteners.

25. An apparatus according to claim 24 wherein the advancing mechanism includes a first advancing mechanism operably connected to the first jaw and movable to advance the first jaw towards the second jaw a first predetermined distance, and a second advancing mechanism operably connected to the first jaw and movable to advance the first jaw a second predetermined distance towards the second jaw subsequent to movement of the first predetermined distance.

26. An apparatus according to claim 25 wherein the first and second advancing mechanisms include first and second ratchet and pawl members, respectively.

27. An apparatus according to claim 24 wherein the advancing mechanism includes a pusher bar pivotably connected at a pivot point to a housing of the apparatus, the pusher bar being operably associated with the first jaw and reciprocatingly pivotable about the axis transverse to the longitudinal axis of the apparatus to advance the first jaw towards the second jaw.

28. An apparatus according to claim 27 wherein the advancing mechanism includes a first advancing mechanism operably connected to the first jaw and movable to advance the first jaw towards the second jaw a first predetermined distance, and a second advancing mechanism operably connected to the first jaw and movable to advance the first jaw towards the second jaw a second predetermined distance.

29. An apparatus according to claim 28 wherein the first and the second advancing mechanisms include first and second ratchet and pawl members, respectively.

30. An apparatus according to claim 29 wherein the first and second pawl members are mounted on the pusher bar, and the first and second ratchet members are operably connected to the first jaw, such that upon reciprocating the pusher bar about the pivot point, the first pawl member engages the first ratchet member to advance the first jaw the first predetermined distance and subsequently the second pawl member engages the second ratchet member to advance the first jaw the second predetermined distance.

31. An apparatus according to claim 24 further comprising a movable rod operably connected to the first jaw such that the movable rod is advanced towards the second jaw as the first jaw is advanced towards the second jaw.

32. An apparatus according to claim 31 further comprising a retaining mechanism, at least a portion of the retaining mechanism being movable from a first non-engaging position to a second position engaging the movable rod to selectively position the first jaw in relation to the second jaw.

33. An apparatus according to claim 32 wherein the retaining mechanism includes a pivotable clamp member having a central throughbore through which the movable rod passes, an edge of the central throughbore engaging the movable rod in the second position of the retaining mechanism.

34. An apparatus according to claim 32 wherein the advancing mechanism includes a pusher bar pivotably connected at a pivot point to a housing of the apparatus, the pusher bar being operably connected to the first jaw, such that upon being pivoted in a first direction about the pivot point, the first jaw is advanced towards the second jaw.

35. An apparatus according to claim 34 further comprising a release mechanism operably associated with the pusher bar, such that upon pivoting the pusher bar in a second direction about the pivot point, the release mechanism is moved into engagement with the retaining mechanism to move the retaining mechanism from the second position to the first position to release the first jaw.

* * * * *